United States Patent [19]
Rankins

[11] Patent Number: 6,017,353
[45] Date of Patent: Jan. 25, 2000

[54] INSTRUMENT FOR REMOVAL OF FOREIGN BODIES FROM THE EAR OR NOSE

[76] Inventor: Robert Rankins, 1166 E. Everett Ave., Fresno, Calif. 93720

[21] Appl. No.: 09/040,513

[22] Filed: Mar. 17, 1998

[51] Int. Cl.[7] .............................. A61F 9/00; A61F 11/00
[52] U.S. Cl. ............................................................ 606/162
[58] Field of Search .................................. 606/162, 161, 606/207

[56] References Cited

U.S. PATENT DOCUMENTS

| | | |
|---|---|---|
| 394,550 | 12/1888 | Ansley . |
| 1,350,123 | 8/1920 | Theodore . |
| 2,116,651 | 2/1938 | Ackerson . |
| 4,174,548 | 11/1979 | Dunn .................................. 15/104.33 |
| 4,575,143 | 3/1986 | Nast . |
| 4,830,002 | 5/1989 | Semm ..................................... 606/207 |

*Primary Examiner*—Michael Buiz
*Assistant Examiner*—Vy Q. Bui
*Attorney, Agent, or Firm*—Richard A. Ryan

[57] ABSTRACT

An instrument for retrieving foreign bodies from an ear or nose canal having a hollow tubular body with a longitudinal passageway therein and a rod with a plurality of flexible members attached at one end. In the closed position, the rod and flexible members are received within the passageway and the flexible members are collapsed against each other. In the open position, the flexible members extend beyond the end of the tubular body and expand apart. The ends of the flexible members have an angled portion for grasping and retrieving the foreign body. In use, the instrument is placed in the ear or nose canal in the closed position. The tubular body is slid towards the rod end of the instrument, causing the flexible members to expand against the ear or nose canal wall. The entire instrument is pushed into the ear or nose canal until the angled portions go beyond the stuck foreign body. The tubular body is then slid forward to trap the foreign body in the flexible members. The instrument and foreign body are pulled from the ear or nose.

14 Claims, 1 Drawing Sheet

INSTRUMENT FOR REMOVAL OF FOREIGN BODIES FROM THE EAR OR NOSE

BACKGROUND OF THE INVENTION

1. Field of the Invention

The field of the present invention relates generally to medical instruments for use in removing objects from inside small, confined and sensitive areas of the human body. In particular, the present invention relates to medical instruments suitable for grasping and removing foreign bodies from the ear or nose canal.

2. Background

A problem frequently encountered by doctors, nurses and emergency personnel, such as emergency medical technicians and the like, is the need to remove foreign bodies that have become lodged in the ear or nose canal. For various reasons, foreign bodies become stuck inside the ear or nose canal and have to be removed by medical personnel. Often the patients who have a need for removal of a foreign body from the ear or nose canal are children who have placed small objects inside their ear or nose. Although the ear and nose canal are very small, a large variety of foreign bodies of varying sizes are removed by medical personnel on an almost daily basis. Due to the small size of the ear and nose canal, there is not much room for medical personnel to manipulate a device inside the canal to grasp and remove a foreign body that is stuck therein. Further compounding the difficulty in removing such foreign bodies is the fact that both the ear and nose canals are relatively sensitive parts of the human body. Needless to say, patients who have a foreign body stuck inside their ear or nose canal tend to be very agitated and anxious regarding its removal, thereby making retrieval of the foreign body even more difficult. This problem is particularly acute in the case of small children.

The current, generally accepted procedure to remove a foreign body from an ear or nose canal consists of using alligator forceps and/or ear loops to remove the item. These devices require visualization of the foreign body during the manipulation of the device inside the ear or nose canal. In addition, because of the relative size and shape of these devices, they do not work well with foreign bodies that are smooth and tightly fitted against the ear or nose canal wall (i.e., such as pellets or BBS). The difficultly with visualization is compounded when the patient is unable or unwilling to remain still during the removal procedure. If the foreign body is not able to be removed by current devices, the patient generally must have surgery to remove the foreign body.

3. Related Art

A number of related art devices exist that are used for grasping and retrieving objects of various sizes and types. Such devices include U.S. Pat. No. 4,575,143 to Nast, U.S. Pat. No. 2,116,651 to Ackerson, U.S. Pat. No. 1,350,123 to Theodore and U.S. Pat. No. 394,550 to Ansley. None of these related art devices solve the problems identified above, which are solved by the present invention. Each of the aforementioned patents present object retrieval devices that are not suitable for use in removing foreign bodies from the ear or nose canal. As such, the inventions set forth in the aforementioned patents, or any derivations thereof, are generally not utilized by medical personnel to remove foreign bodies from the ear or nose canal.

The Nast patent discloses a pick-up tool having a reciprocating means, magnetic device and gripping mechanism that is designed to be utilized by mechanics for the retrieval of small objects from confined places. The Nast device provides sufficient extension control and gripping to grasp metallic items. However, the device is neither sized nor designed to operate inside the ear or nose canal. The Ackerson patent discloses tongs that are primarily designed to grab and retrieve cherries, olives and similar objects from inside a jar or bottle. The Theodore patent discloses an article handler that attaches to devices suitable for clamping on to and retrieving articles off of shelves. The Ansley patent discloses a fruit picker that is suitable for picking fruit off of trees. As with the Nast patent, the Ackerson, Theodore and Ansley patents disclose devices that are suitable for the purposes of their respective designs, but which are not suitable for use to retrieve foreign bodies from within the confined, sensitive area of the nose or ear canal.

SUMMARY OF THE INVENTION

The instrument for retrieving foreign bodies from the ear or nose canal of the present invention solves the problems identified above. That is to say, the present invention provides an instrument that allows medical personnel to remove foreign objects from within the confined, sensitive areas of the ear and nose canal without injuring the ear or nose canal or risk pushing the foreign body further up the ear or nose canal.

In the primary embodiment of the present invention, the instrument comprises an elongated rod received within the longitudinal passageway of a hollow tubular body. Connected to one end of the rod is a plurality of flexible members that have an angled portion at each of the distal ends thereof. In the preferred embodiment, the tubular body has a circular cross-section and the rod has three flexible members connected thereto, although other configurations are possible and can function equally as well. The rod and flexible members slide inside the passageway of the tubular body.

In the closed condition, the rod extends out one end of the tubular body and the flexible members are folded together and received within, either partially or completely, the passageway of the tubular body. To open the flexible members, the tubular body is slid toward the rod end of the instrument or the rod is pushed through the passageway of the tubular body. Either way, the flexible members extend past the tubular body and expand circumferentially (i.e., spread apart). To close the flexible members the tubular body is slid toward the end of the instrument with the flexible members or the rod is pulled through the tubular body toward the user (typically the user will be located on the rod side of the instrument looking into the ear or nose canal).

By holding on to the outer surface of the tubular body and the proximal end of the rod, the user of the instrument can closely control the relative movements of the tubular body and that of the rod and flexible member combination. In this manner, the user can slowly move the flexible members up the ear or nose canal to ensure that the flexible members will move as gently as possible through the ear or nose canal and past the foreign body. Close control of the movement of the flexible members through the ear or nose canal is required so that the lining of the ear or nose canal is not injured, or further injured as the case may be, and the foreign body is not pushed further up the ear or nose canal.

The angled portions at the distal end of the flexible members are bent inward at an angle that enables the distal end to slide past the foreign body and which is sufficient to ensure that the foreign body is grabbed or pulled by the angled portions when the instrument is withdrawn from the ear or nose canal. The inventor has found that an angle of approximately 140 degrees (measured from the longitudinal axis of the flexible members) works well, although angles from about 110 to 150 degrees will work equally as well. The shape and configuration of the angled portion of the flexible members is also important for ensuring that the instrument does not injure the lining of the ear or nose canal or cause pain to the patient.

Due to the nature of the movement of the instrument of the present invention, it is not necessary for the medical personnel or other user of the instrument to be able to visualize the foreign body or the ear or nose canal. Once the tubular body is placed inside the ear or nose canal, the flexible fingers can be moved up the canal and around the foreign body using the feel of instrument to let the user know that the angled portion of the flexible fingers have gone beyond the foreign body. Once the angled portions have gone past and are in position behind the foreign body, the user can retrieve the foreign body by merely pulling the instrument out of the patient's ear.

Accordingly, the primary objective of the present invention is to provide an instrument suitable for use by medical personnel and others to remove a foreign body from an ear or nose canal.

It is also an important objective of the present invention to provide an instrument that utilizes a hollow tubular body with a rod having a plurality of flexible members connected at one end received within the tubular body for grasping and retrieving foreign bodies stuck in the ear or nose canal.

It is also an important objective of the present invention to provide an instrument having flexible members with angled portions at the distal ends thereof that are suitable for sliding along the ear or nose canal without injuring the canal or causing pain to the individual and for retrieving a foreign body stuck therein.

It is also an objective of the present invention to provide an instrument that allows the user thereof to be able to closely control the movement of the instrument through the ear or nose canal and past a foreign body stuck therein.

Yet another important objective of the present invention is to provide an instrument that allows the user thereof to move the instrument through the ear or nose canal and past a foreign body stuck therein without being able to visualize that movement or the foreign body.

BRIEF DESCRIPTION OF THE DRAWINGS

In the drawings which illustrate the best modes presently contemplated for carrying out the present invention.

DETAILED DESCRIPTION OF THE PREFERRED EMBODIMENTS

Figure 1:
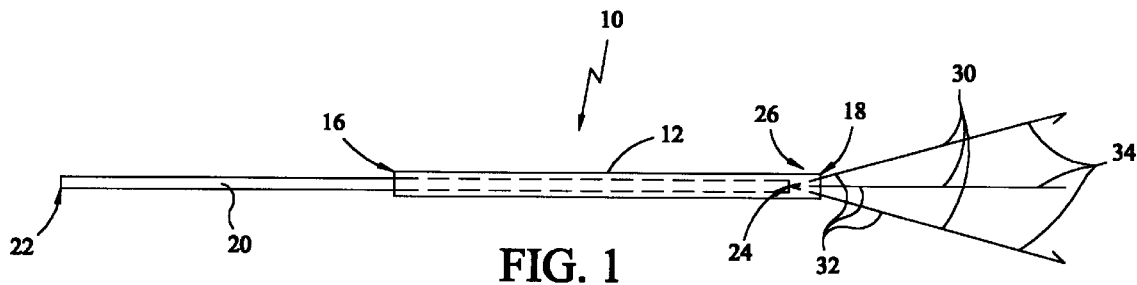
FIG. 1 is a side view of the present invention showing the flexible members in the extended and expanded position.

With reference to the figures where like elements have been given like numerical designations to facilitate the reader's understanding of the present invention, and particularly with reference to the embodiment of the present invention illustrated in FIGS. 1 through 4, the preferred embodiment of the present invention is set forth below. The instrument for retrieving foreign bodies from the ear or nose canal, designated generally as 10, is designed to be placed inside the ear or nose canal and grasp and then facilitate the retrieval of a foreign body stuck therein.

Instrument 10 has a hollow tubular body 12 having longitudinal passageway 14 therethrough and first opening 16 and opposing second opening 18 at the ends thereof. Rod 20, having a first end 22 and second end 24, is received in passageway 14. Tubular body 12 is shown in the accompanying figures as a having a circular cross-section, however, it is understood that tubular body 12 can have other configurations, such as square, rectangular or triangular cross-section, and function equally as well as the circular cross-section shown. Tubular body 12 should be sufficiently rigid to allow instrument 10 to be inserted in an ear or nose canal and be controlled by the user.

Figure 2:
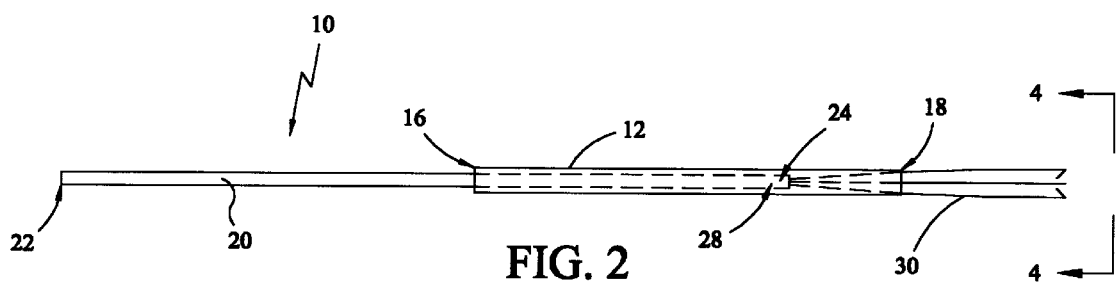
FIG. 2 is a side view of the present invention showing the flexible members in the withdrawn and closed position.

Rod 20 should be sized and configured to slide within tubular body 12 from first position 26 at or near second opening 18 to a second position 28 located towards first opening 16. Second position 28 will be located at or near first opening 16 or somewhere between first opening 16 and second opening 18 depending upon the length of flexible members 30 and/or the length of flexible members 30 that remain outside tubular body 12 when the instrument 10 is in the closed position, as shown in FIG. 2. To assist the user with holding on to rod 20 during the procedure to remove a foreign body from the ear or nose canal, the portion of rod 20 near first end 22 can be covered or coated with a material or substance (not shown) that enhances the user's ability to grip rod 20. The subject material or substance should be firmly attached to rod 20 and provide an essentially non-slip surface for the user. Examples of such material or substances include tape, plastic, stick coating and the like.

Instrument 10 can be designed such that flexible members 30 are entirely contained within tubular body 12 when the instrument 10 is in the closed condition or a portion of the flexible members 30 can remain outside of tubular body 12, as shown in FIG. 2. To prevent second end 24 of rod 20 from being pushed or going beyond second opening 18 of tubular body 12, instrument 10 can have a stopping mechanism at the place where second end 24 would exit second opening 18. One example of such a stopping mechanism is the use of an inwardly folded lip on second opening 18 that prevents second end 24 of rod 20 from going beyond second opening 18 by narrowing passageway 14. Such a stopping mechanism can also be used at first opening 16 to prevent second end 24 of rod 20 from being pulled out of tubular body 12.

Figure 3:
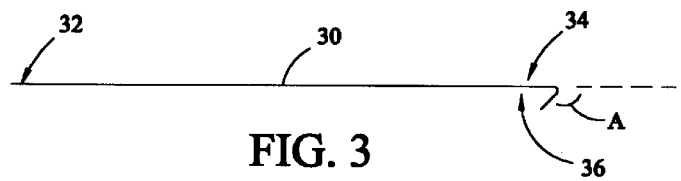
FIG. 3 is a side view one of the flexible members of the present invention showing the angled end.
Figure 4:
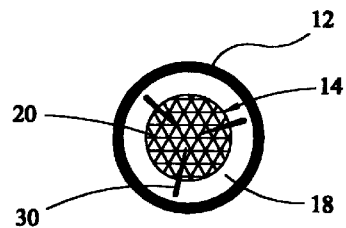
FIG. 4 is an end view of the present invention taken along lines 4—4 of FIG. 2.

A plurality of flexible members 30 connect at their proximal ends 32 to second end 24 of rod 20 using glue, solder, wire or any other connecting method commonly known for connecting wire members to an end of a rod. Although FIGS. 1, 3 and 4 show the use of three flexible members 30, it should be understood that two or more flexible members 30 can accomplish the objectives set forth herein. Flexible members 30 should be sufficiently flexible to allow flexible members 30 to follow the contour of the ear or nose canal and slide past a foreign body located therein. In the preferred embodiment, flexible members 30 extend approximately 45 degrees from the longitudinal axis of tubular body 12 when the flexible members 30 are fully extended (i.e., when second end 24 of rod 20 is at first position 26). The amount of angle which flexible members 30 extend would need to be adjusted for the stiffness of the material used for flexible members 30 (the stiffer the material, the less angle is necessary or desired due to the need to follow the contour of the ear or nose canal). Flexible members 30 can be made of wire, such as spring wire or other types of wire, or metal strips. The material used for flexible members 30, as well as the entire instrument 10, should be suitable for sterilization by conventional methods.

At the distal end 34 of each of flexible members 30, flexible member is bent inwardly to form angled portion 36. In the preferred embodiment, angled portion 36 of flexible members 30 are contained in the last 1 mm of length of flexible members 30 and are bent inwardly approximately 140 degrees (shown as angle "A" in FIG. 3) from the longitudinal axis of flexible members 30. The inventor has found that an angle of 140 degrees allows angled portion 36 to slide past most foreign bodies stuck in an ear or nose canal without undue difficultly or risk of pushing the foreign body further up the canal. This inwardly bent angle also works well as a grasping mechanism for retrieving the foreign body out of the ear or nose canal. Other lengths of angled portion 36 and inwardly bent angles can work equally as well, provided that angled portion 36 is able to move between a foreign body and the ear or nose canal wall and is able to securely pull a foreign body that is stuck in the ear or nose canal out of the ear or nose.

In use, the patient is first reviewed by the doctor or other medical personnel and it is determined that a foreign body is stuck in the ear or nose canal. If this is the case, the end of instrument 10 having flexible members 30, in its closed condition as shown in FIG. 2, is placed part way inside the ear or nose canal. Once inside the canal, tubular body 12 is slid towards the rod end of instrument 10, causing rod 20 to move from second position 28 to first position 26 and flexible members 30 to extend beyond second opening 18 and expand circumferentially along the sides of the ear or nose canal. Once opened, entire instrument 10 is advanced up the ear or nose canal, causing flexible members 30 to follow the shape of the canal and angled portions 36 thereon to slide past the foreign body. With angled portions 36 beyond the foreign body, tubular body 12 is advanced towards the flexible member end of instrument 10, causing second end 24 of rod to advance from first position 26 to second position 28 and flexible members 30 to contract and close around the foreign body. Once the foreign body is trapped within angled portions 36 of flexible members 30, instrument 10 is withdrawn from the ear or nose canal, thereby pulling the foreign body out with instrument 10.

While there is shown and described herein certain specific alternative forms of the invention, it will be readily apparent to those skilled in the art that the invention is not so limited, but is susceptible to various modifications and rearrangements in design and materials without departing from the spirit and scope of the invention. In particular, it should be noted that the present invention is subject to modification with regard to the dimensional relationships set forth herein and modifications in assembly, materials, size, shape, and use.

What is claimed is:

1. An instrument for removing foreign bodies from the ear or nose canal, comprising:

a hollow tubular body having a longitudinal passageway therethrough and opposing first and second openings at the ends of said tubular body;

an elongated rod received within said passageway of said tubular body, said rod having a first end and a second end, said second end of said rod moveable from a first position near said second opening of said tubular body to a second position toward said first opening of said tubular body;

a plurality of flexible members each connected at a proximal end thereof to said second end of said rod, said flexible members each having a distal end opposite said proximal end, said flexible members receivable within said passageway of said tubular body through said second opening when said rod is moved from said first position to said second position, said flexible members expandable outside of said tubular body upon movement of said second end of said rod from said second position to said first position;

prehensile means at said distal end of each of said flexible members each having an angled portion for grasping foreign bodies in the ear or nose canal when said flexible members are received within said passageway of said tubular body; and stopping means at the conjunction of said second end of said rod with said second opening of said tubular body for stopping said second end of said rod from going beyond said second opening when said rod is moved from said second position to said first position.

2. The instrument according to claim 1, wherein said tubular body is rigid.

3. The instrument according to claim 1, wherein said prehensile means comprises an angled portion at said distal end of each of said flexible members.

4. The instrument according to claim 3, wherein said angled portion is bent inward at an angle of approximately 140 degrees from the longitudinal axis of said flexible members.

5. The instrument according to claim 1, wherein said prehensile means is located within the approximately 1 mm distal most portion of said distal end of said flexible members.

6. The instrument according to claim 1 further comprising a grasping means on said rod near said first end for the user of said instrument to firmly grasp said rod.

7. The instrument according to claim 1, wherein said flexible members expand approximately 45 degrees from the longitudinal axis of said passageway when said rod is moved from said second position to said first position.

8. The instrument according to claim 1, wherein said tubular body, said rod, said flexible members and said prehensile means are made of material that can be sterilized.

9. An instrument for removing foreign bodies from the ear or nose canal, comprising:

a rigid hollow tubular body having a longitudinal passageway therethrough and opposing first and second openings at the ends of said tubular body;

an elongated rod received within said passageway of said tubular body, said rod having a first end and a second end, said second end of said rod moveable from a first position near said second opening of said tubular body to a second position toward said first opening of said tubular body;

a plurality of flexible members each connected at a proximal end thereof to said second end of said rod, said flexible members each having a distal end opposite said proximal end, said flexible members receivable within said passageway of said tubular body through said second opening when said rod is moved from said first position to said second position, said flexible members expandable outside of said tubular body upon movement of said second end of said rod from said second position to said first position; and an angled portion at said distal end of each of said flexible members located within the approximately 1 mm distal most portion of said distal end of said flexible members for grasping foreign bodies in the ear or nose canal when said flexible members are received within said passageway of said tubular body, said angled portion bent inwardly from the longitudinal axis of said flexible members at an angle of approximately 140 degrees.

10. An instrument for removing foreign bodies from the ear or nose canal, comprising:

a hollow tubular body having a longitudinal passageway therethrough and opposing first and second openings at the ends of said tubular body;

an elongated rod received within said passageway of said tubular body, said rod having a first end and a second end, said second end of said rod moveable from a first position near said second opening of said tubular body to a second position toward said first opening of said tubular body;

a plurality of flexible members each connected at a proximal end thereof to said second end of said rod, said flexible members each having a distal end opposite said proximal end, said flexible members receivable within said passageway of said tubular body through said second opening when said rod is moved from said first position to said second position, said flexible members expandable outside of said tubular body upon movement of said second end of said rod from said second position to said first position;

prehensile means at said distal end of each of said flexible members each having an angled portion for grasping foreign bodies in the ear or nose canal when said flexible members are received within said passageway of said tubular body; and stopping means at the conjunction of said second end of said rod with said first opening of said tubular body for stopping said second end of said rod from going beyond said second opening when said rod is moved from said second position to said first position.

11. The instrument according to claim 10, wherein said prehensile means comprises an angled portion at said distal end of each of said flexible members, said angled portion bent inward at an angle of approximately 140 degrees from the longitudinal axis of said flexible members.

12. The instrument according to claim 10, wherein said prehensile means is located within the approximately 1 mm distal most portion of said distal end of said flexible members.

13. The instrument according to claim 10 further comprising a grasping means on said rod near said first end for the user of said instrument to firmly grasp said rod.

14. The instrument according to claim 10, wherein said flexible members expand approximately 45 degrees from the longitudinal axis of said passageway when said rod is moved from said second position to said first position.

* * * * *

UNITED STATES PATENT AND TRADEMARK OFFICE
CERTIFICATE OF CORRECTION

PATENT NO. : 6,017,353
DATED : January 25, 2000
INVENTOR(S) : Robert Rankins

It is certified that error appears in the above-identified patent and that said Letters Patent is hereby corrected as shown below:

<u>Column 8,</u>
Line 9, "second" should read -- first --.
Line 10, "second" should read -- first -- and "first" should read -- second --.

Signed and Sealed this

Twenty-first Day of August, 2001

Attest:

*Nicholas P. Godici*

NICHOLAS P. GODICI
*Attesting Officer*        *Acting Director of the United States Patent and Trademark Office*